United States Patent [19]

Battaglia, Jr.

[11] Patent Number: 5,345,931
[45] Date of Patent: Sep. 13, 1994

[54] ENDOTRACHEAL TUBE HOLDER

[75] Inventor: Anthony J. Battaglia, Jr., Pittsburgh, Pa.

[73] Assignee: Marc J. Schnedierman, Caraopolis, Pa.

[21] Appl. No.: 119,355

[22] Filed: Sep. 9, 1993

[51] Int. Cl.⁵ .................... A61M 25/02; A61M 16/00
[52] U.S. Cl. .................... 128/207.17; 128/DIG. 26; 604/179
[58] Field of Search .................. 128/200.24, 200.26, 128/207.14, 207.15, 207.17, DIG. 26; 604/174, 178, 179

[56]         References Cited
       U.S. PATENT DOCUMENTS

| | | | |
|---|---|---|---|
| 3,017,887 | 1/1962 | Heyer | 128/DIG. 26 X |
| 3,713,448 | 1/1973 | Arrott | 128/DIG. 26 X |
| 3,760,811 | 9/1973 | Andrew | 128/207.17 |
| 3,774,616 | 11/1973 | White et al. | 128/200.26 |
| 3,946,742 | 3/1976 | Eross | 128/207.17 |
| 3,976,080 | 8/1976 | Bornhorst et al. | 604/179 |
| 3,987,798 | 10/1976 | McGinnis | 128/207.17 |
| 3,993,081 | 11/1976 | Cussell | 128/207.14 |
| 4,141,524 | 2/1979 | Corvese | 248/70 |
| 4,223,671 | 9/1980 | Muto | 128/200.26 |
| 4,249,529 | 2/1981 | Nestor et al. | 128/207.17 |
| 4,282,871 | 8/1981 | Chodorow et al. | 128/207.18 |
| 4,326,515 | 4/1982 | Shaffer et al. | 128/207.17 |
| 4,344,428 | 8/1982 | Sherman | 128/207.14 |
| 4,351,331 | 9/1982 | Gereg | 128/207.17 |
| 4,378,012 | 3/1983 | Brown | 128/207.17 |
| 4,392,857 | 7/1983 | Beran | 604/179 |
| 4,437,463 | 3/1984 | Ackerman | 128/207.17 |
| 4,449,527 | 5/1984 | Hinton | 128/207.17 |
| 4,520,813 | 6/1985 | Young | 128/207.17 |
| 4,537,192 | 8/1985 | Foster | 128/207.17 |
| 4,548,200 | 10/1985 | Wapner | 128/207.17 |
| 4,571,245 | 2/1986 | Hubbard et al. | 604/179 |
| 4,598,705 | 7/1986 | Lichtenberger | 128/200.26 |
| 4,622,034 | 11/1986 | Shattuck | 604/179 |
| 4,660,555 | 4/1987 | Payton | 128/207.18 |
| 4,739,757 | 4/1988 | Edwards | 128/207.18 |
| 4,744,358 | 5/1988 | McGinnis | 128/207.17 |
| 4,774,946 | 10/1988 | Ackerman et al. | 128/207.18 |
| 5,009,227 | 4/1991 | Nieuwstad | 128/207.17 |
| 5,167,630 | 12/1992 | Paul | 604/179 |

OTHER PUBLICATIONS

SecureEasy ® advertising brochure number 246017 of Respironics Inc. ® dated Jan. 3, 1991 (1 page).

Primary Examiner—Edgar S. Burr
Assistant Examiner—Eric P. Raciti
Attorney, Agent, or Firm—Webb Ziesenheim Bruening Logsdon Orkin & Hanson

[57]              ABSTRACT

An endotracheal tube holder includes a faceplate configured to be positioned against a patient's face and adjacent the patient's mouth. The faceplate includes an elongated guide track in a guide track portion which is configured to be positioned beneath the patient's mouth. The endotracheal tube holder also includes an endotracheal tube platform attached to the guide track portion of the faceplate and configured to carry an endotracheal tube thereon. A slide is provided for moving the endotracheal tube platform along the guide track. In addition, a lock is included for locking the endotracheal tube platform to one of a plurality of locations along the guide track.

17 Claims, 5 Drawing Sheets

FIG_6

FIG_7

FIG_8

FIG. 9

FIG. 10 ly in the art. A complicated
ENDOTRACHEAL TUBE HOLDER

BACKGROUND OF THE INVENTION

1. Field of the Invention

This invention is related to endotracheal tube holders which hold an endotracheal tube in a patient's mouth during mechanical ventilation.

2. Description of the Prior Art

A patient may require an endotracheal tube to assist with the patient's breathing. An elongated tube is passed through a patient's mouth and into the trachea, and an inflatable exterior cuff on the tube is used to seal the trachea about the tube. The external end of the endotracheal tube is connected to a ventilation system in a known manner.

It is important to physically secure the endotracheal tube to the patient to keep the tube from being accidentally removed, crimped or the like. Adhesive tape has been used to secure the tube, but the tape is uncomfortable for a patient and has a tendency to traumatize a patient's skin. A number of endotracheal tube holding devices have been proposed in the art. A complicated structure has been proposed in U.S. Pat. No. 4,744,358, and sold by Respironics Inc. as the "SecureEasy ®" endotracheal tube holder. While this device does adequately hold an endotracheal tube in place, its complicated headgear/strap arrangement makes it inconvenient for use by nursing personnel. Other endotracheal tube holders are shown in U.S. Pat. Nos. 3,760,811; 3,774,616; 3,976,080; 3,946,742; 3,993,081; 4,249,529; 4,326,515; 4,344,428; 4,351,331; 4,378,012; 4,437,463; 4,449,527; 4,520,813; 4,537,192; 4,548,200; 4,622,034 and 5,009,227. Other medical tube holding devices are shown in U.S. Pat. Nos. 3,987,798; 4,282,871; 4,571,245; 4,660,555; 4,739,757 and 4,774,946.

The devices shown in the above-identified patents have a common characteristic in that the endotracheal tube is held in one position and cannot be readily moved. When the tube is held in a fixed position beyond a certain period of time, damage to a patient's mouth and/or lip tissue occurs. This is a particular problem with critical care and other patients who require the use of an endotracheal tube over an extended treatment period.

It is, therefore, an object of the present invention to provide an endotracheal tube holder which permits the tube to be moved to different positions with respect to a patient's mouth and/or lips.

U.S. Pat. No. 4,223,671 describes an endotracheal tube holder which permits a limited degree of motion of the tube. However, this device requires considerable force to move the tube holder, offers little degree of movement, and includes a faceplate which completely covers and contacts a patient's lips. Thus, tissue damage to the patient's lips is not avoided. Moreover, access to the patient's mouth is not possible without completely removing the tube holder.

It is, therefore, a further object of the present invention to provide an endotracheal tube holder which permits considerable movement of the tube holder, and avoids mouth and lip tissue damage, yet leaves a patient's mouth and lips substantially uncovered and accessible. It is an object of the present invention to provide an endotracheal tube holder which is easy to install and use, is comfortable to the patient, and permits easy movement of the tube between a large number of different positions without disturbing the patient to any significant degree.

SUMMARY OF THE INVENTION

Accordingly, I have developed an endotracheal tube holder which includes a faceplate configured to be positioned against a patient's face and adjacent the patient's mouth. The faceplate includes an elongated guide track in a guide track portion therein, with the guide track portion configured to be positioned beneath the patient's mouth. The endotracheal tube holder also includes an endotracheal tube platform attached to the guide track portion of the faceplate and configured to carry an endotracheal tube thereon. A slide means provided for moving the endotracheal tube platform along the guide track. In addition, a locking means is included for locking the endotracheal tube platform to one of a plurality of locations along the guide track.

The faceplate can include a first side portion and a second side portion spaced therefrom. The guide track portion extends between the side portions along their lower edges. The side portions are substantially taller than the narrower guide track portion. The faceplate forms a U-shaped structure which is configured such that the side portions contact a patient's cheeks on opposite sides of the patient's mouth and the guide track portion contacts the patient's chin.

A resilient bite block can be attached to and aligned with the tube platform and configured to carry an endotracheal tube thereon. The bite block can include a pair of opposed resilient arms extending outwardly from a rear surface of the tube platform. A securement means, such as a pair of opposed locking tabs, can be provided on the tube platform for securing an endotracheal tube thereto. A mounting harness is attached to the faceplate and wraps around the patient's neck to securely attach the endotracheal tube holder to the patient's face. The mounting harness can include a neck brace and a pair of straps attached at opposite sides thereof, with the first and second side portions of the faceplate each including a strap receiving slot to which the mounting harness straps are attached.

The slide means can include a guide member having a base positioned within the guide track portion and slideable along the guide track, and having a head attached to the guide member and extending through the guide slot. The tube platform is attached to a free end of the guide member extending beyond an outer surface of the guide track portion. The tube platform can include a pivot shaft attached to a lower surface thereof and extending perpendicularly therefrom. The pivot shaft passes through a hole in the free end of the head of the guide member. The locking means can include a locking lever pivotally mounted on the pivot shaft and on the head of the guide member. The locking lever is moveable from a first position which permits free movement of the guide member along the guide track to a second position which locks the guide member to the guide track portion. The locking lever can include a handle and at least one cam member, preferably two spaced cam members, attached thereto. If a pair of cam members is used, they are positioned on opposite surfaces of the head of the guide member. Each cam member includes a flat surface opposite the handle and oriented toward the guide track portion. Each cam member includes aligned, eccentric holes which are configured to receive the pivot shaft of the tube platform. In the first locking lever position, the flat surfaces of the cam members are rotated away from the guide track portion. In the second locking lever position, the flat surfaces of the cam members are rotated against the outer surface of the guide track portion and the base of the guide member is drawn into engaging contact with an inner surface of the guide track portion.

In a preferred embodiment, the guide track includes a plurality of inwardly oriented teeth and the base of the guide member includes at least one tooth, and preferably two teeth, on an outer surface thereof and oriented toward the teeth on the guide track. When the locking lever is moved to the second locking lever position, the teeth on the base of the guide member engage the teeth on the guide track. The teeth on the base of the guide member are moved out of engagement with the teeth on the guide track when the locking lever is moved to the first locking lever position.

The flat surfaces of the locking lever cam members can include a compression member attached thereto. In addition, a plurality of cushion members can be attached to an inner surface of the faceplate.

DESCRIPTION OF THE PREFERRED EMBODIMENTS

An endotracheal tube holder 10 in accordance with the present invention is shown in FIGS. 1-9. The endotracheal tube holder 10 includes a rigid faceplate 12 and a flexible mounting harness 14 attached thereto. The faceplate 12 is a rigid plastic framework which includes a first side portion 16, a second side portion 18 spaced therefrom and a guide track portion 20 attached to and extending between the first and second side portions 16 and 18. As will be explained hereinafter in more detail, a tube platform 22, configured to receive and hold an endotracheal tube, is attached to the guide track portion 20 of the faceplate 12 on an outer surface thereof.

The side portions 16 and 18 are substantially taller than the narrower guide track portion 20, which preferably extends between said side portions 16, 18 at their lower edges, with the faceplate 12 forming a U-shaped structure when viewed from the front. The faceplate 12 is preferably curved inwardly to conform to a patient's face, with the side portions 16, 18 configured to rest on a patient's cheeks and with the guide track portion 20 configured to rest along the patient's chin, beneath the patient's lower lip. The side portions 16, 18 have strap receiving slots 24, 26, respectively, therethrough. The first side portion 16 has raised rib 28 integral therewith and extending outwardly from the outer surface of the faceplate 12, along an outer edge of the first side portion 16 and adjacent strap slot 24. Similarly, the second side portion 18 has raised rib 30 along an outer edge thereof and adjacent strap slot 26. Raised ribs 28 and 30 provide additional strength to the faceplate 12 along its outer edges, yet enable the faceplate 12 to be molded in a lightweight structure. To further lighten the faceplate 12 and provide additional ventilation to a patient's face, the first side portion 16 can include a plurality of vents 32 and cross ribs 34 adjacent its inner edge, and the second side portion 18 can include a plurality of vents 36 and cross ribs 38 adjacent its inner edge.

The inner surface of the faceplate 12 can be covered with cushioning foam rubber padding to provide a comfortable fit when the faceplate 12 is positioned adjacent a patient's face. In the embodiment shown herein, cushion 39 is attached to an inner surface of the first side portion 16 above slot 24 and cushion 40 is attached to an inner surface of the second side portion 18 above slot 26. Cushion 41 is attached to an inner surface of the guide track portion 20 and extends to the inner surface of the first side portion 16 beneath slot 24 and to the inner surface of the second side portion 18 beneath slot 26.

Figure 1:
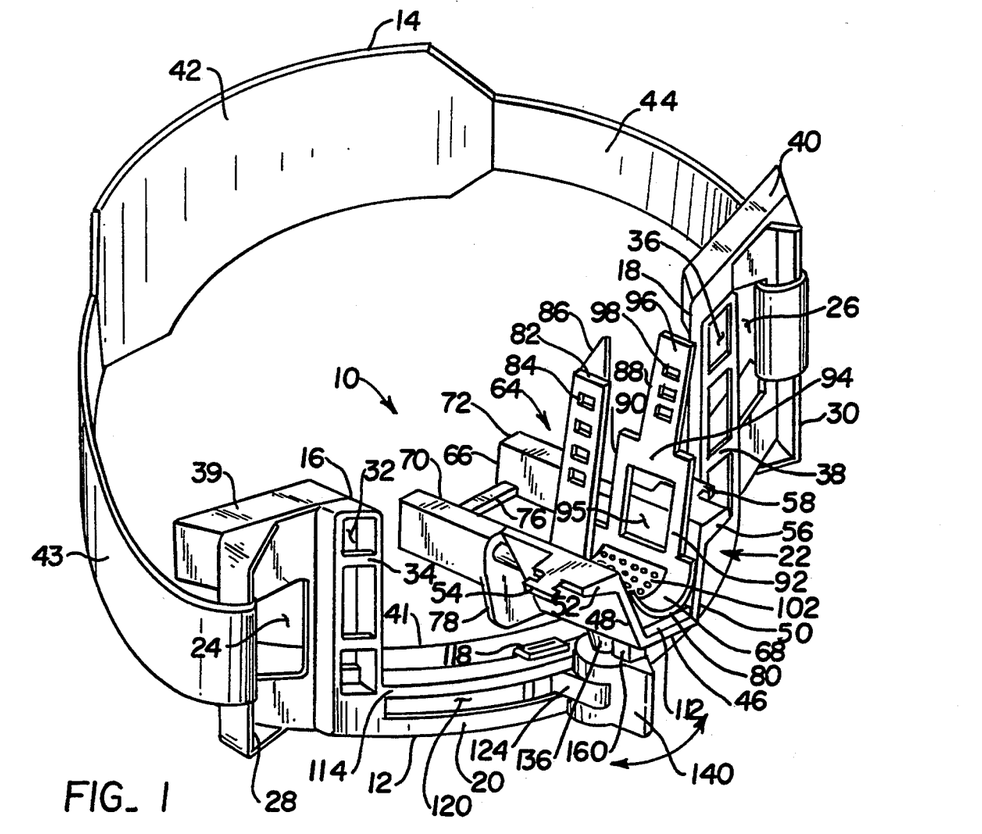
FIG. 1 is a perspective view of one embodiment of an endotracheal tube holder in accordance with the present invention and with a mounting harness attached thereto.
Figure 2:
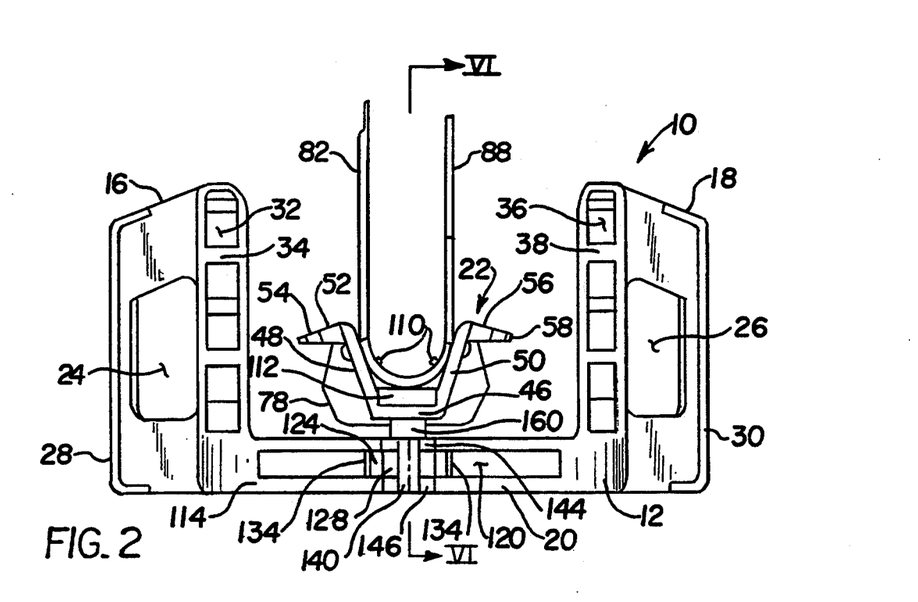
FIG. 2 is a front view of the endotracheal tube holder shown in FIG. 1 with the mounting harness removed.
Figure 3:
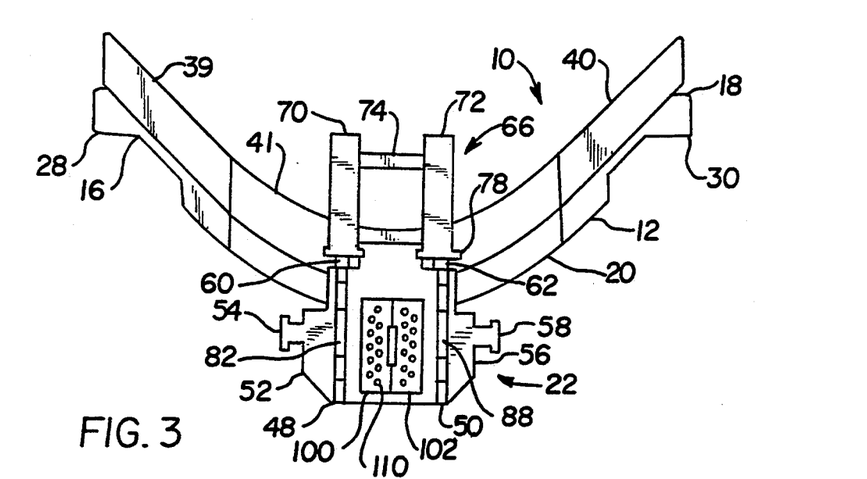
FIG. 3 is a top view of the endotracheal tube holder shown in FIG. 2.
Figure 4:
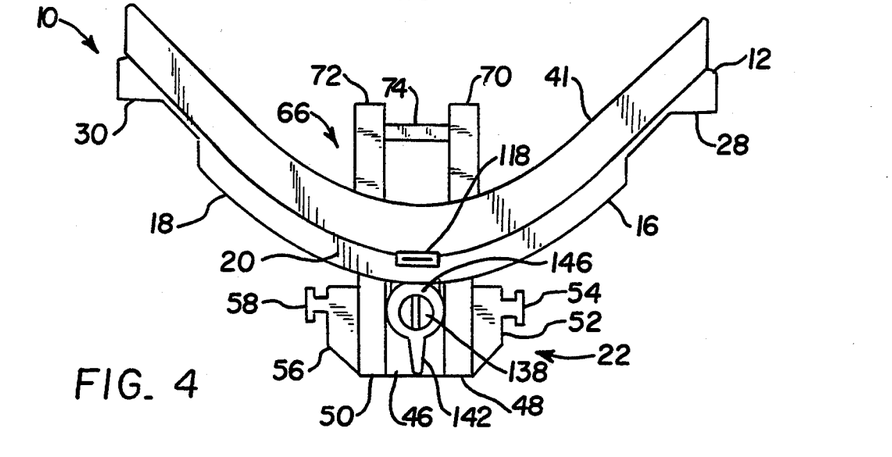
FIG. 4 is a bottom view of the endotracheal tube holder shown in FIG. 2.
Figure 5:
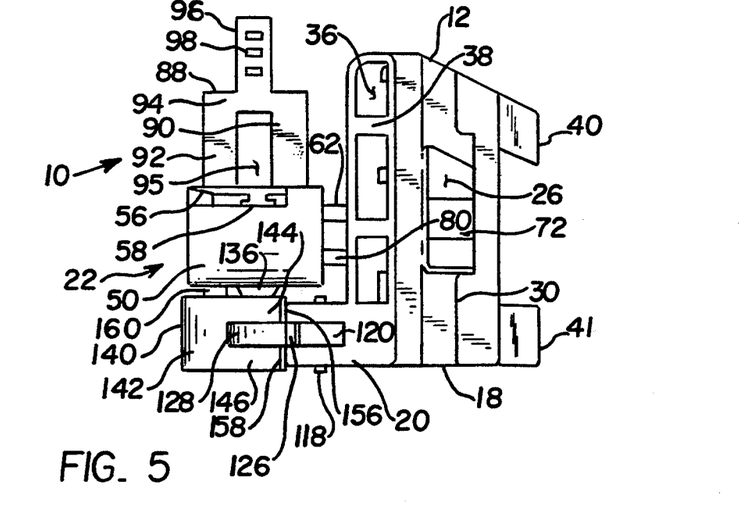
FIG. 5 is a side view of the endotracheal tube holder shown in FIG. 2.

The mounting harness 14 includes a wide neck brace 42, preferably padded on its inner surface, and narrower straps 43 and 44 attached at opposite sides of the neck brace 42 and extending outwardly therefrom. The free ends of straps 43 and 44 on the mounting harness 14 include a closure mechanism, such as a hook and loop closure material, to enable the straps 43 and 44 to be removably attached to the faceplate 12. As shown in FIG. 1, strap 43 is passed through slot 24 in the first side portion 16 of the faceplate 12 and around raised rib 28, and is then secured in place. Similarly, strap 44 is passed through slot 26 in the second side portion 18 of the faceplate 12 and around raised rib 30, and is then secured in place.

Figure 9:
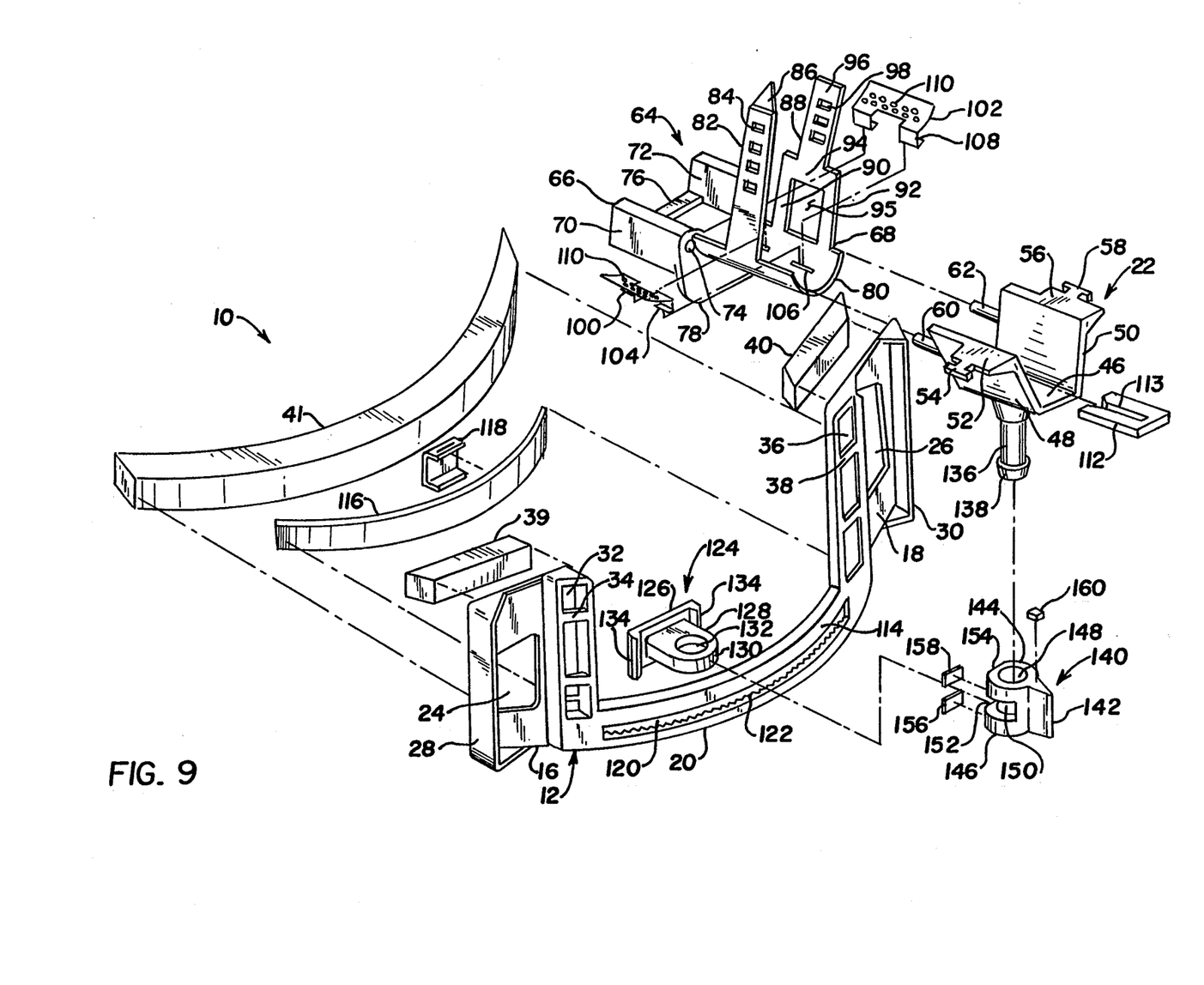
FIG. 9 is an exploded view of the endotracheal tube holder shown in FIG. 2.

The tube platform 22 is an elongated, open-topped, U-shaped rigid, preferably plastic, structure including a flat platform base 46 and upstanding and opposed flat sidewalls 48 and 50 attached thereto. Sidewalls 48 and 50 preferably flare outwardly at an angle of about 15° from vertical as they extend upwardly from the platform base 46. Flange 52 extends outwardly from sidewall 48 along an upper edge and terminates in an attachment prong 54. Flange 56 extends outwardly from sidewall 50 and terminates in an attachment prong 58. Elongated pins 60 and 62 are attached to an inner edge of sidewalls 48 and 50, respectively, and extend outwardly perpendicularly thereto and parallel with the platform base 46.

A resilient member 64 is carried by the tube platform 22 and includes, in an integral structure, a bite block 66 at one end and a tube retainer 68 at the other end. The bite block 66 includes spaced apart arms 70 and 72 which are slideably mounted on pins 60 and 62, respectively, by elongated holes internal to arms 70 and 72. Hole 74 in arm 70 is visible in FIG. 9. A similar hole is provided in arm 72 but is not visible in the drawings. A tube supporting cross bar 76 extends between the lower edges of arms 70 and 72 at their ends away from the base 46 of the tube platform 22. A flat lip shield 78 extends downwardly from and between arms 70 and 72 at their ends where the bite block 66 meets the tube retainer 68.

The tube retainer 68 has a rectangular base 80 which is positioned within and curves to contact the tube platform 22 above an upper surface of the platform base 46 and along inner surfaces of sidewalls 48 and 50. Locking tab 82 is a flat, rectangular member attached to one side of base 80 adjacent sidewall 48 and extends outwardly therefrom and perpendicular thereto. Locking tab 82 includes a plurality of slots 84 therein and terminates in a pointed tip 86. Locking tab 88 is attached to an opposite side of base 80 adjacent sidewall 50 and extends outwardly therefrom and perpendicular thereto. Locking tab 88 includes spaced apart legs 90 and 92 attached to base 80 and cross member 94 attached to and extending between the ends of legs 90 and 92 opposite base 80. Legs 90 and 92, cross member 94 and base 80 define opening 95 therein. Tab 96 of locking tab 88 is attached to cross member 94 opposite opening 95 and includes a plurality of slots 98 therethrough.

Metal gripping members 100 and 102 are positioned on an upper surface of the base 80 of the tube retainer 68 and aid in affixing the resilient member 64 to the tube platform 22. Gripping member 100 has two mounting flanges 104 which pass through corresponding and aligned holes 106 in base 80. Gripping member 102 has two mounting flanges 108 which likewise pass through holes 106 in base 80. The outer surfaces of gripping members 100 and 102 preferably include a plurality of upwardly oriented and sharp projections 110. A U-shaped, plastic retaining clip 112 having central slot 113 is positioned beneath the lower surface of base 80 and slot 113 engages flanges 104 and 108 to securely attach the gripping members 100 and 102 to base 80. The arms 70 and 72 of the bite block 66 are pushed onto pins 60 and 62, respectively, and the retaining clip 112 is affixed by adhesive or the like to the platform base 46. In this manner, the resilient member 64 is securely affixed to the tube platform 22.

The guide track portion 20 of the faceplate 12 is hollow and includes an outer section 114 integral with the first and second sides 16 and 18, respectively, and having a U-shaped cross section. The guide track portion 20 also includes a curved back plate 116 covering the inner, open portion of the U-shaped outer section 114. The back plate 116 is attached to the outer section 114 of the guide track portion 20 by a plastic, U-shaped clip 118 passing around the back plate 116 and attached to the outer section 114. Cushion 41 is attached to both the back plate 116 and clip 118. An elongated, rectangular guide slot or track 120 is formed in the outer section 114 through an outer wall of the guide track portion 20 and extends therethrough to an interior thereof. The guide track 120 extends substantially along the length of the guide track portion 20, and between the first and second sides 16 and 18. The opposed inner surfaces of the outer section 114 adjacent to and defining the guide track 120 include a plurality of inwardly facing teeth 122.

A guide member 124 is a plastic, T-shaped structure which is positioned within the guide track portion 20 of the faceplate 12 and extends outwardly therefrom through the guide track 120. The guide member includes a flat, rectangular base 126 which fits within the hollow interior of the guide track portion 20 and a flat head 128 which is attached to an outer surface of base 126 and extends outwardly and perpendicularly therefrom through the guide track 120 and parallel thereto.

The free end 130 of head 128 is rounded and hole 132 extends through the head 128 near its free end 130 and beyond the outer surface of the guide track portion 20 of the faceplate 12. The outer surface of the base 126 of the guide member 124 has a pair of spaced apart and elongated teeth 134 on opposite sides of the head 128 and extending along the outer sides of base 126. Teeth 134 on base 126 are configured to mesh with teeth 122 along the guide track 120 when the guide member 124 is positioned thereagainst.

A pivot shaft 136 is attached to a lower surface of the base 46 of the tube platform 22 and extends outwardly and downwardly therefrom and perpendicular thereto. The pivot shaft 136 terminates at its lower end in a wider locking flange 138. A plastic locking lever 140 includes a handle 142 and a pair of spaced apart, parallel and coaxial cams 144 and 146 attached to the handle 142. Cams 144 and 146 have holes 148 and 150, respectively, passing therethrough and aligned with each other. Cams 144 and 146 are generally circular in shape and holes 148 and 150 are eccentrically positioned therein. Flat surfaces 152 and 154 are provided on the outer edges of cams 144 and 146, respectively, opposite the handle 142. The centers of holes 148 and 150 are oriented closer to the handle 142 than they are to flat surfaces 152 and 154 of the cams 144 and 146. Flat compression members 156 and 158 can be provided on flat surfaces 152 and 154, respectively, and flat compression member 160 can be provided on an upper surface of the handle 142 adjacent cam 144.

To attach the tube platform 22 to the faceplate 12, the locking lever 140 is positioned on the head 128 of the guide member 124, with cams 144 and 146 sandwiching the guide member 124 therebetween, with holes 132, 148 and 150 aligned, and with the flat surfaces 152 and 154 of cams 144 and 146 oriented toward the faceplate 12. The tube platform 22 is positioned above the guide track portion 20 of the faceplate 12 and between the first and second sides 16 and 18, with the bite block 66 oriented inwardly of the inner surface of the guide track portion 20 and with the platform base 46 oriented over the locking lever 140. The pivot shaft 136 is passed through holes 132, 148 and 150 and the locking flange 138 locks the tube platform 22, the guide member 124 and the locking lever 140 together in a single structure and to the faceplate 12.

The tube platform 22/guide member 124/locking lever 140 combination can be moved along the guide track 120 in the guide track portion 20 to any of a plurality of desired locations thereon and locked in place. When the locking lever 140 is rotated with the flat surfaces 152, 154 of the cams 144, 146, respectively, adjacent and contacting the outer surface of the guide track portion 20 of the faceplate 12, the base 126 of the guide member 124 is drawn into contact with the inner surface of the outer section 114 of the guide track portion 20. In this manner, the teeth 134 on the guide member 124 contact the teeth 122 in the guide track 120 and lock the guide member 124 thereto in a particular location. This configuration is shown specifically in FIGS. 6 and 7.

Figure 6:
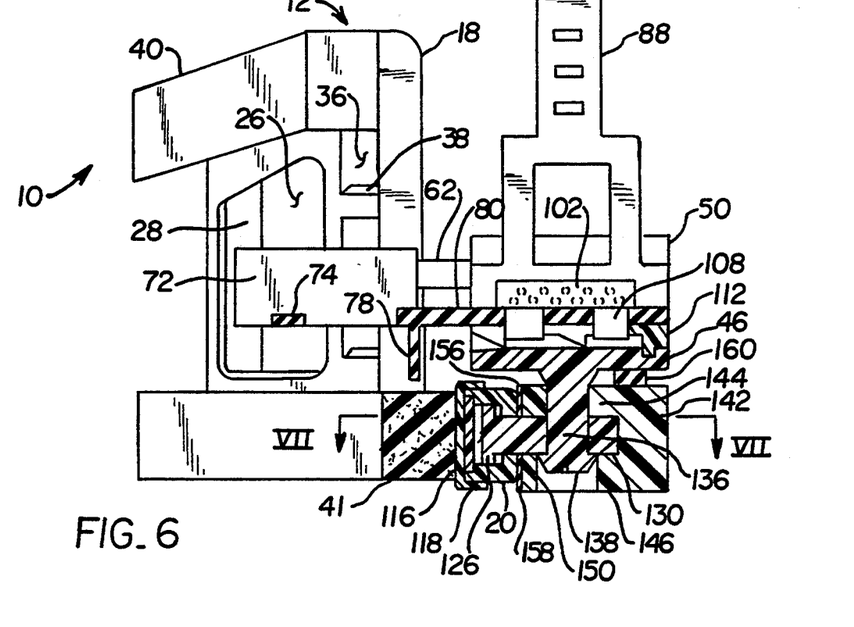
FIG. 6 is a section taken along lines VI—VI in FIG. 2.
Figure 7:
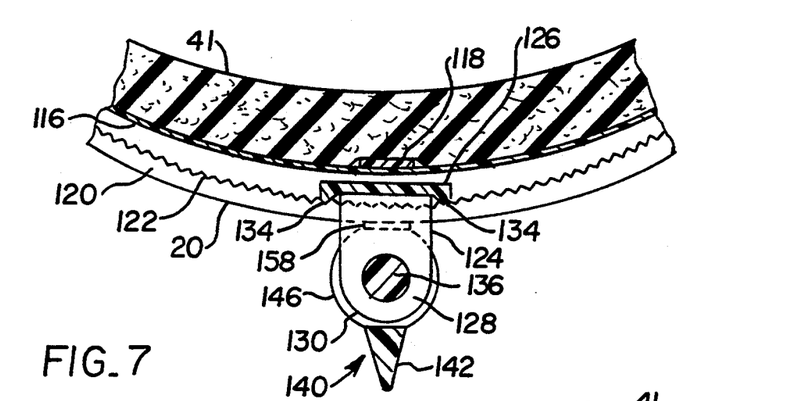
FIG. 7 is a section taken along lines VII—VII in FIG. 6 and showing a locking lever in a locked position.
Figure 8:
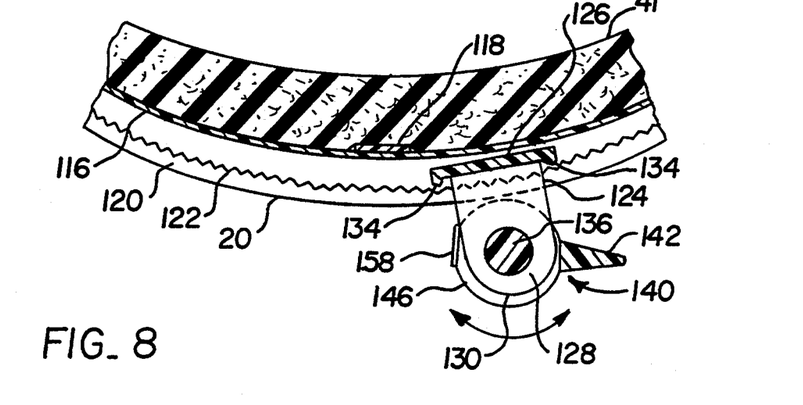
FIG. 8 is a section similar to FIG. 7 and showing the locking lever in an unlocked position.

By grasping the handle 142 on the locking lever 140, and rotating it left or right about an axis passing through the pivot shaft 136, the flat surfaces 152, 154 on cams 144, 146 will be moved out of contact with the outer surface of the guide track portion 20. This rotation of the locking lever 140 draws the flat surfaces 152, 154 out of engaging contact due to the eccentricity of the holes 148, 150 in the cams 144, 146. Thereafter, the teeth 134 on the base 126 of the guide member 124 are moved out of engagement with the teeth 122 of the guide track 120. This configuration is shown specifically in FIG. 8. At this point, the guide member 124/locking lever 140 combination is not locked in place within the guide track 120 and can be moved to another desired location along a curved axis extending through the guide track 120. This movement simultaneously moves the tube platform 22 to the same position since the tube platform 22 is attached to the guide member 124 through the locking lever 140 as discussed above. After the guide member 124/locking lever 140 combination is moved to the new location, the locking lever 140 is rotated once again to position the flat surfaces 152, 154 of the cams 144, 146 in engaging contact with the outer surface of the guide track portion 20 as shown in FIGS. 6 and 7. The tube platform 22 will remain in this new position until the steps discussed above are repeated.

The compression members 156, 158 on the cams 144, 146 help to insure a tight fit when the locking lever 140 is moved to the locked position shown in FIG. 7. The compression member 160 on the upper surface of the handle 142 of the locking lever 140 helps to insure a tight fit between the locking lever 140 and the tube platform 22 located thereabove. Although it is desirable to permit the tube platform 22 to pivot about an axis extending through the pivot shaft 136, so that the angle of entry of the tube platform 22 into a patient's mouth can be adjusted, it is also desirable to reduce significant free play therebetween through the use of compression member 160.

Figure 10:
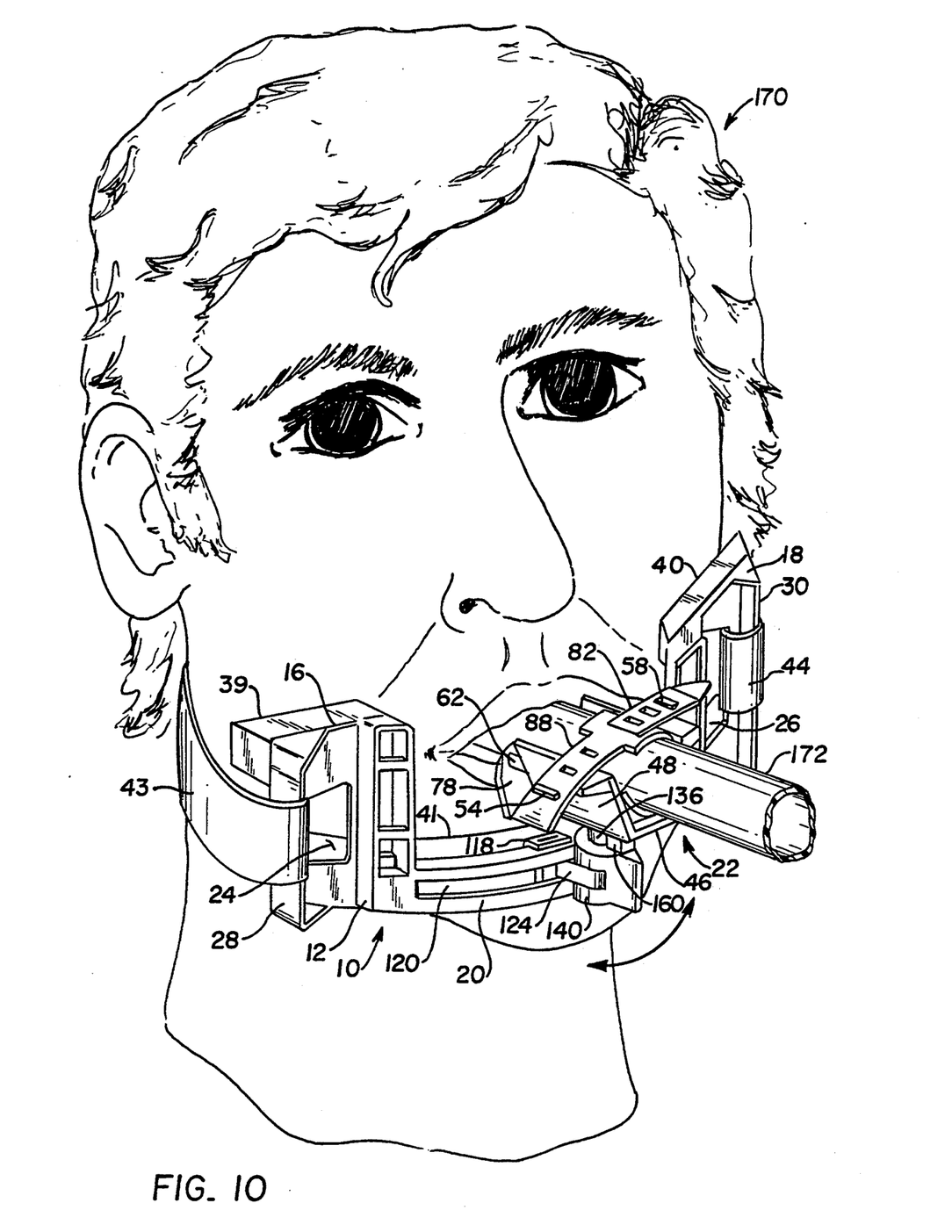
FIG. 10 is a perspective view of a patient's head showing the endotracheal tube holder of FIGS. 1-9 attached thereto and holding an endotracheal tube.

The use of the endotracheal tube holder 10 in accordance with the present invention with a patient 170 is shown in connection with FIG. 10. The faceplate 12 is positioned against the patient's face with cushions 39, 40 and 41 contacting the face of the patient 170, with the first side portion 16 and second side portion 18 of the faceplate 12 on opposite sides of the patient's mouth, and with the guide track portion 20 extending along the patient's chin and beneath the patient's lower lip. The bite block 66 of the tube platform 22 is positioned within a patient's mouth. Straps 43 and 44 are attached to the faceplate 12 by passing them through strap slots 24 and 26 and around raised ribs 28 and 30, respectively, and attaching the free ends of straps 43 and 44 thereto. The neck brace 42 of the mounting harness 14 is positioned comfortably behind the neck of the patient and straps 43 and 44 are adjusted appropriately to provide a secure, yet comfortable fit of the faceplate 12 to the patient 170. An endotracheal tube 172, inserted through the patient's mouth and down the patient's trachea, is laid along the tube platform 22 between arms 70 and 72 of the bite block 66 and above cross bar 76, above the gripping members 100 and 102 within the sidewalls 48 and 50, and above the base 46 of the tube platform 22. It is preferred that the arms 70 and 72 of the bite block 66 be higher than the diameter of the endotracheal tube 172 so that the patient 170 can bite down on the bite block 66 without unduly compressing the endotracheal tube 172. The projections 110 on the outer surface of the gripping members 100 and 102 help to keep the endotracheal tube 172 from sliding along the tube platform 22. The locking tabs 82 and 88 are used to securely affix the endotracheal tube 172 to the tube platform 22 and within sidewalls 48 and 50. Initially, locking tab 82 is wrapped around the endotracheal tube 172 and the tip 86 of locking tab 82 is passed through opening 95 of locking tab 88. Locking tab 82 is then stretched over flange 56 on sidewall 50 and an appropriate one of slots 84 of locking tab 82 is connected to prong 58 on flange 56 to secure locking tab 82 thereto. Thereafter, tab 96 of locking tab 88 is wrapped about the endotracheal tube 172, over locking tab 82 and over flange 52 and on sidewall 48. An appropriate one of slots 98 in locking tab 88 is connected to prong 54 on flange 52 to secure locking tab 88 thereto. In this manner, the endotracheal tube 172 is securely positioned to a patient 170 and at a particular location with respect to the patient's mouth.

After a particular period of time, the tube platform 22 can be moved to a different position as discussed above to thereby move the endotracheal tube 172 and the bite block 66 to another location with respect to the patient's mouth and lips. In this manner, medical personnel can assure that the tube platform 22 does not rest against the patient in the same location for an unduly extended period of time which, in turn, prevents tissue damage to the lip and mouth cells. Movement of the endotracheal tube 172 from one position to another can be made easily and without significantly disturbing the patient. Moreover, most of the patient's mouth remains uncovered and reduces total stress thereon and permits easy access to the patient's mouth for other medical treatments. By permitting the tube platform 22 to rotate about an axis passing through the pivot shaft 136, positioning of the endotracheal tube 172 within the patient's mouth in a new position is facilitated.

Although the present invention discloses the use of a toothed track and complementary toothed guide member to hold the tube platform 22 in a particular position on the faceplate 12, the present invention is not so limited. Any type of locking arrangement would be satisfactory as long as the tube platform 22 can be moved to different positions along the guide track 120 and locked in place to the faceplate 12.

It can be seen that the endotracheal tube holder described herein permits the tube to be moved to different positions with respect to the patient's mouth and lips. The tube can be moved between a large number of positions, yet leaves the patient's mouth uncovered and accessible. The tube holder is easy to use and install and is comfortable to the patient, and a tube attached thereto can be moved with little or no disturbance to the patient.

Having described above the presently preferred embodiments of the present invention, it is to be understood that it may be otherwise embodied within the scope of the appended claims.

I claim:
1. An endotracheal tube holder comprising:
 a) a faceplate configured to be positioned against a patient's face and adjacent the patient's mouth, said faceplate including a guide track portion having an elongated guide track therein, with said guide track portion configured to be positioned beneath the patient's mouth;
 b) an endotracheal tube platform attached to the guide track portion of said faceplate and configured to carry an endotracheal tube thereon;
 c) slide means for moving said endotracheal tube platform along said guide track; and
 d) locking means for locking said endotracheal tube plateform to one of a plurality of locations along said guide track.
2. The endotracheal tube holder of claim 1 wherein said faceplate includes a first side portion and a second side portion spaced therefrom, said side portions having lower edges, with said guide track portion extending between said side portions along their lower edges, with said side portions substantially taller than said guide track portion, and with said faceplate forming a U-shaped structure and configured such that the side portions contact a patient's cheeks on opposite sides of the patient's mouth and such that the guide track portion contacts the patient's chin.

3. The endotracheal tube holder of claim 1 further including a resilient bite block attached to and aligned with said tube platform and configured to carry an endotracheal tube thereon.

4. The endotracheal tube holder of claim 3 wherein said bite block includes a pair of opposed resilient arms extending outwardly from a rear surface of said tube platform.

5. The endotracheal tube holder of claim 1 further including securement means on said tube platform for securing an endotracheal tube to the tube platform.

6. The endotracheal tube holder of claim 5 wherein said securement means includes a pair of opposed locking tabs which are configured to wrap around the endotracheal tube and lock on opposed sides of said tube platform.

7. The endotracheal tube holder of claim 1 further including a mounting harness attached to said faceplate and configured to be wrapped around the patient's neck and securely attach said endotracheal tube holder to the patient's face.

8. The endotracheal tube holder of claim 7 wherein said mounting harness includes a neck brace and a pair of straps attached at opposite sides thereof, with the first and second side portions each including a strap receiving slot therein to which said mounting harness straps are attached.

9. The endotracheal tube holder of claim 1 wherein said slide means includes a guide member having a base positioned within said guide track portion and slideable along said guide track, and having a head attached to said guide member and extending through said guide track, with said tube platform attached to a free end of said guide member extending beyond an outer surface of said guide track portion.

10. The endotracheal tube holder of claim 9 wherein said tube platform includes a pivot shaft attached to a lower surface thereof and extending perpendicularly therefrom, and with said pivot shaft passing through a hole in the free end of the head of said guide member.

11. The endotracheal tube holder of claim 10 wherein said locking means includes a locking lever pivotally mounted on said pivot shaft and on the head of said guide member, with said locking lever moveable from a first position which permits free movement of said guide member along said guide track to a second position which locks said guide member to said guide track portion.

12. The endotracheal tube holder of claim 11 wherein said locking lever includes a handle and at least one cam member attached thereto and positioned adjacent the head of said guide member, with said cam including an eccentric hole therethrough and receiving the pivot shaft of said tube platform, with said cam including a flat surface opposite said handle and oriented toward said guide track portion, wherein in said first locking lever position the flat surface of the cam is rotated away from said guide track portion, said guide track portion having an inner surface, and wherein in said second locking lever position the flat surface of the cam is rotated against the outer surface of the guide track portion and the base of the guide member is drawn into engaging contact with an inner surface of the guide track portion.

13. The endotracheal tube holder of claim 12 wherein the locking lever includes a pair of cams attached to said handle and positioned on opposite surfaces of the head of said guide member, with each cam including aligned, eccentric holes therethrough and receiving the pivot shaft of said tube platform, and with each cam including flat surfaces opposite said handle and oriented toward said guide track portion.

14. The endotracheal tube holder of claim 13 wherein said guide track includes a plurality of inwardly oriented teeth and said base of said guide member includes at least one tooth on an outer surface thereof and oriented toward the teeth on said guide track, whereby the tooth on the base of said guide member engages the teeth on the guide track when the locking lever is moved to the second locking lever position, and the tooth on the base of said guide member moves out of engagement with the teeth on the guide track when the locking lever is moved to the first locking lever position.

15. The endotracheal tube holder of claim 14 wherein the base of said guide member includes two such teeth, one on each side of said head attached thereto.

16. The endotracheal tube holder of claim 13 wherein the flat surfaces of said locking lever cams includes a compression member attached thereto.

17. The endotracheal tube holder of claim 1 further including a plurality of cushion members attached to an inner surface of said faceplate.

* * * * *

UNITED STATES PATENT AND TRADEMARK OFFICE
CERTIFICATE OF CORRECTION

PATENT NO. : 5,345,931
DATED : September 13, 1994
INVENTOR(S) : Anthony J. Battaglia, Jr.

It is certified that error appears in the above-indentified patent and that said Letters Patent is hereby corrected as shown below:

Column 2, line 14, after "means" insert --is--.

Column 8, Claim 1, line 65, "plateform" should read -- platform--.

Signed and Sealed this

Twenty-fourth Day of January, 1995

Attest:

BRUCE LEHMAN

Attesting Officer

Commissioner of Patents and Trademarks